United States Patent [19]

Dragan et al.

[11] Patent Number: 4,654,027
[45] Date of Patent: Mar. 31, 1987

[54] VASCULAR DILATING DEVICE

[76] Inventors: William B. Dragan, 85 Burr St., Easton, Conn. 06612; John Discko, Jr., 50 Laura Rd., Hamden, Conn. 06514

[21] Appl. No.: 792,750

[22] Filed: Oct. 30, 1985

[51] Int. Cl.$^4$ ............................................. A61M 29/00
[52] U.S. Cl. .................................... 604/99; 604/247; 604/248; 137/614.2
[58] Field of Search ...................... 604/96, 97, 99, 118, 604/121, 207, 208, 209, 218, 246, 247, 248; 137/599, 614.2

[56] References Cited

U.S. PATENT DOCUMENTS

| | | | |
|---|---|---|---|
| 458,774 | 9/1891 | Lottridge | 604/248 |
| 1,014,228 | 1/1912 | Kellogg | 604/99 |
| 2,074,401 | 3/1937 | Kauzal | 604/208 |
| 2,737,199 | 3/1956 | Ingram | 137/599 |
| 2,742,901 | 4/1956 | Krauthamer | 604/121 |
| 3,833,000 | 9/1974 | Bridgman | 604/248 |
| 4,198,756 | 4/1980 | Dragan | 433/90 |
| 4,332,254 | 6/1982 | Lundquist | 128/344 |
| 4,370,982 | 2/1983 | Reilly | 604/99 |
| 4,384,853 | 1/1982 | Welsh | 433/90 |
| 4,439,185 | 3/1984 | Lundquist | 604/97 |
| 4,472,141 | 9/1984 | Dragan | 604/232 |

OTHER PUBLICATIONS

Cook, "Dilation Balloon Inflation Pistol", 1985, 4 pages.

Bard, "USCI Intraoperative Angioplasty Balloon Catheters", 4 pages, undated.

Primary Examiner—C. Fred Rosenbaum
Assistant Examiner—Gene B. Kartchner
Attorney, Agent, or Firm—Arthur T. Fattibene

[57] ABSTRACT

A vascular dilating device for performing a coronary angioplasty procedure that includes a tubular barrel defining a reservoir for containing a supply of actuating fluid and having a plunger and connected piston reciprocally disposed within the reservoir. The outlet of the reservoir is connected to a valve assembly having an outlet to which a balloon catheter is connected. The valve assembly includes a control valve and a unidirectional valve which are co-operatively associated for directing fluid from the reservoir to the balloon catheter in one direction only when the control valve is disposed in a balloon inflating position and the handle is actuated to advance the plunger. A by-pass is also provided in the valve assembly to reverse the fluid flow from the balloon catheter to the reservoir when the control valve is disposed in a second or balloon deflating position. The handle construction includes a actuating lever member disposed in bearing or driving relationship to the plunger so as to impart a mechanical advantage necessary to develope the desired or optimum pressures. A pressure gage is operatively connected to the valve assembly for indicating the pressure of the fluid acting on the balloon catheter.

22 Claims, 12 Drawing Figures

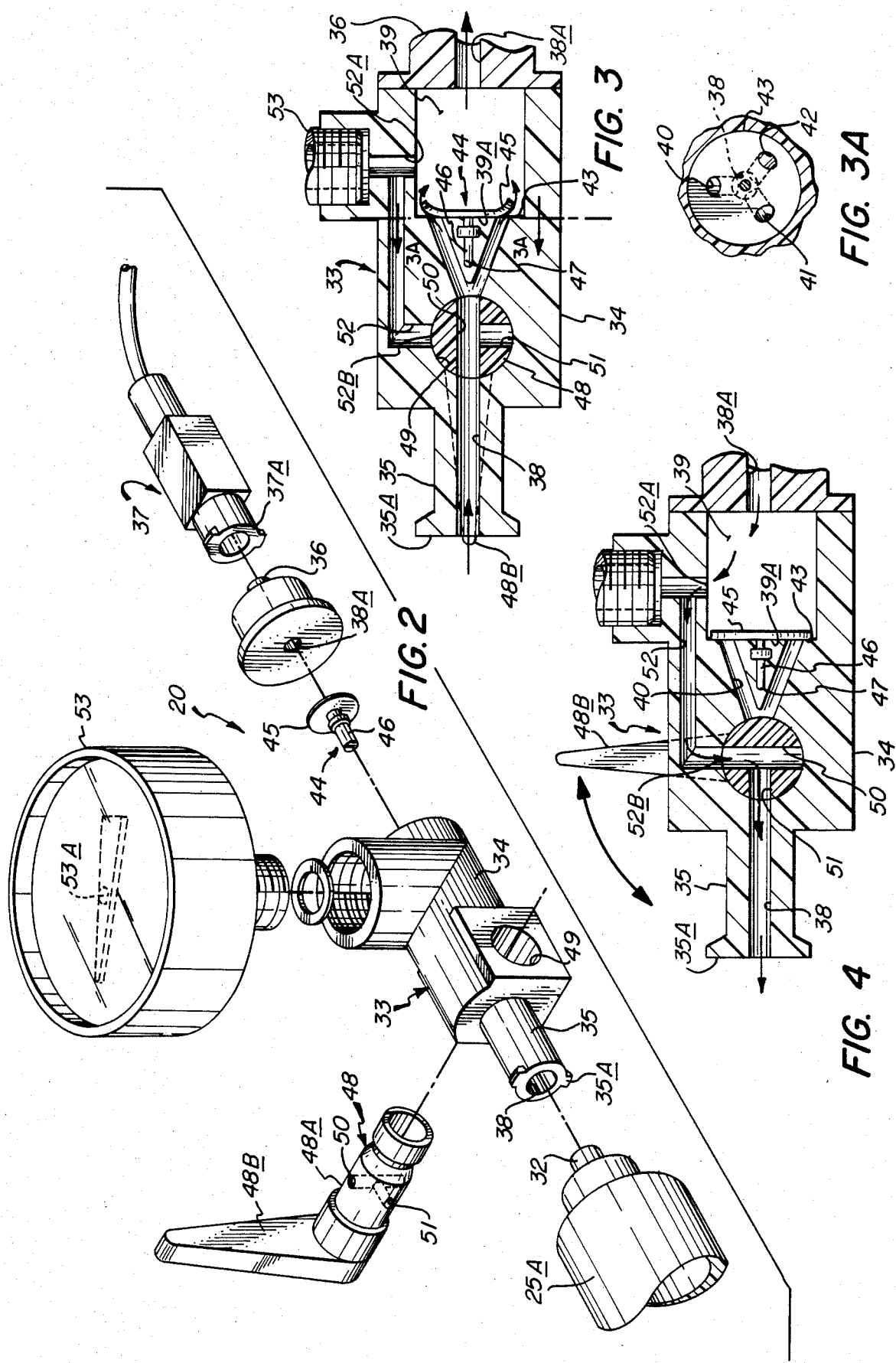

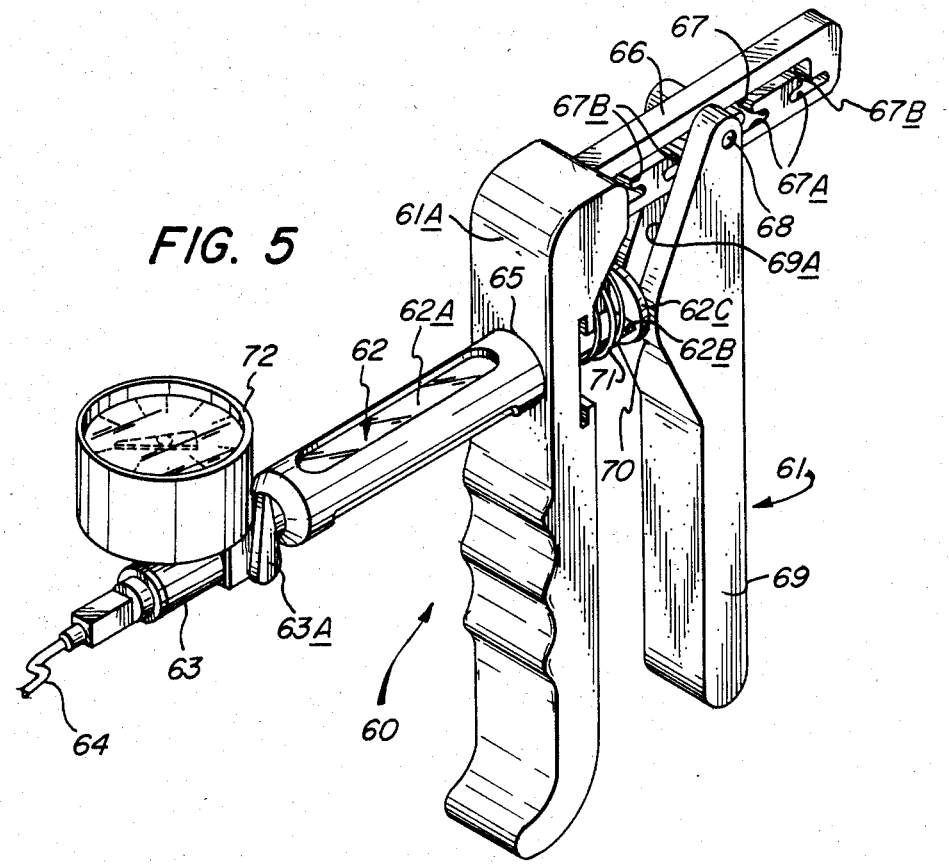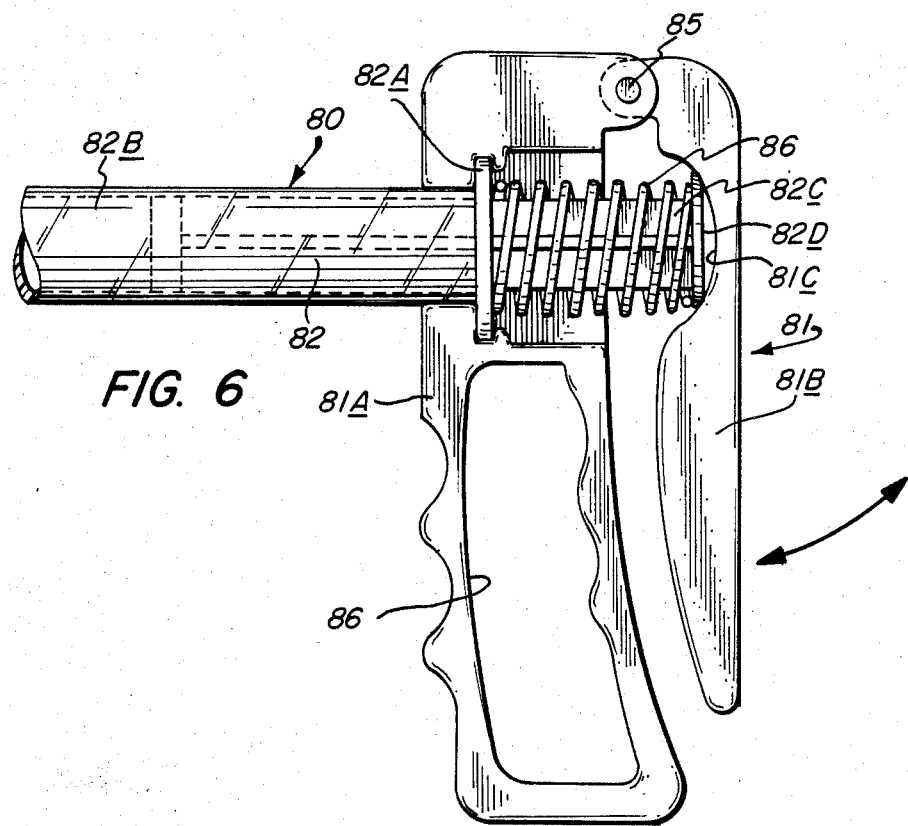

VASCULAR DILATING DEVICE

FIELD OF INVENTION

This invention is directed to a vascular dilating device for performing a coronary angioplasty procedure.

PRIOR ART AND PROBLEM

Angioplasty is a relatively recent technique for the treatment of cardiovascular disease caused by atherosclerosis. The origin of the technique is attributed to Drs. Charles Dotter and Melvin Judkins who initially used progressively larger catheters to open up a blocked leg artery. Later a German cardiologist improved the technique by using minature balloon catheters. The first known human coronary angioplastic procedure occurred in September of 1977.

Since then efforts have been made to develop suitable instrumentation to perfect the angioplastic technique, which has several distinct advantage over heart by-pass surgery which number among them shorter hospital stays, less costly procedure, less traumatic procedure, shorter recuperative time and safer future repeatability.

One such known instrumentation is a device made by Advanced Cardiovascular Systems known as the INDIFLATOR as disclosed in U.S. Pat. No. 4,439,185. This device is basically a simple syringe having an in line pressure gauge, and enlarged finger grips formed on the body of the syringe and associated plunger to help in developing the pressures necessary to perform the angioplastic procedure. The construction of the device was such that it was extremely difficult to generate pressures in excess of 150 psi; as the arrangement lacks any mechanical advantage, and its operation in practice generally required the use of both hands to develop the desired pressures. Also the ability to deflate the balloon catheter as quickly as desired was lacking.

Another known device is made by C. R. Bard. It is generally similar in function to that of the foregoing described INDIFLATOR in that it also utilizes a simple syringe with an attached pressure gauge.

Since another known device is a relatively large gun shaped ratchet driven piston device manufactured by Cook. It is used with a 0.10 cc disposable B-D syringe, the plunger of which is ratchet driven. This device when fitted with syringe, pressure gauge and balloon catheter is extremely large, and relatively high incremental rises in pressure result due to ratchet increments. Such relatively large incremental rises in pressure are undesirable in a delicate angioplastic procedure where very small incremental increases in pressures are frequently desired.

Another known device is disclosed in U.S. Pat. No. 4,332,254. This device is relatively complex in that it requires separate primary and secondary pumps assemblies and two distinct fluid mediums.

OBJECTS

An object of this invention is to provide a vascular dilating device that is rendered relatively simple in construction and positive in operation.

Another object is to provide a vascular dilating device that is inexpensive and rendered readily disposable after use in a given angioplastic procedure.

Another object is to provide a vascular dilating device having a built in mechanical advantage so as to enable an operator to attain the desired high pressures with a minimum of effort.

Another object is to provide an vascular dilating device by which the operator can effectively control the increases in pressure in very small incremental amounts as desired and to maintain such pressure without effort on the part of the operator.

Another object is to provide a vascular dilating device that can be effectively operated with one hand by the operator.

Another object is to provide a vascular dilating device that can create a negative pressure so as to effect immediate deflation of the balloon catheter.

Another object is to provide a vascular dilating device capable of easily developing operating pressures as high as 450 psi simply, quickly and effortlessly.

SUMMARY OF THE INVENTION

The foregoing objects and other features and advantages are attained by a vascular dilating device utilizing a syringe having a tubular barrel to define a reservoir for containing a predetermined amount of actuating fluid, e.g. a radiographic contrast liquid, and a plunger and associated piston for expressing the fluid therefrom during an angioplastic procedure. Connected in communication with the outlet end of the syringe or tubular barrel is a balloon catheter of known construction. Disposed between the outlet of the syringe barrel and the associated balloon catheter is a valve assembly for controlling the fluid flow between the syringe barrel and the balloon catheter and for maintaining the pressure in the balloon catheter. The valve assembly includes a unidirectional valve co-operatively associated with a control valve arranged so that when the control valve is disposed is a first position and the plunger is actuated to express the fluid, the fluid flow is directed through the associated unidirectional valve to inflate the balloon catheter accordingly. The arrangement is such that the back pressure of the fluid in the balloon catheter acting on the unidirectional valve automatically maintains the pressure in the balloon catheter, until released by the operator. To release the fluid pressure in the balloon catheter, the control valve is disposed in a second position. In this position the pressure in the inflated balloon catheter is immediately released by means of a by-pass which is opened when the control valve is moved to its second position.

In another embodiment of the invention, the unidirection valve is incorporated in the control valve in lieu of the by-pass so that the fluid flow between the syringe barrel and the catheter can be readily reversed depending upon the position of the control valve.

The present invention also contemplates a handle construction connected to the syringe barrel for rendering one hand operation of the vascular dilating device. The handle construction includes a pistol grip construction having a fixed handle member connected to the syringe barrel or a housing for receiving the syringe barrel; and an operating handle or lever pivotally connected to the fixed handle member. The operating lever is disposed in bearing relationship to the plunger and imparts a mechanical advantage thereto when the operating lever is squeezed relative to the fixed handle member and causes the plunger and associated piston to be displaced accordingly. If desired, a spring or other suitable biasing member is operatively connected to the plunger for normally biasing the plunger in engagement with the operating lever or handle member. A pressure gauge may be operatively connected to the outlet end of the valve assembly for indicating the fluid pressure acting in the balloon catheter.

The present invention further contemplates several embodiments of varying handle constructions and/or valve assemblies which may be variously combined with the syringe portion of the vascular dilating device.

FEATURES

A feature of this invention resides in the provision of a vascular dilating device having a valve assembly which includes a unidirectional valve interposed between the syringe barrel and the associated balloon catheter which allows the balloon catheter to be progressively inflated by small incremental pressures and whereby such pressures can be automatically maintained without effort on the part of the operator.

Another feature resides in the provision of a pistol grip type handle construction which is operatively associated with the plunger of the syringe assembly whereby the device can be readily operated by one hand.

Another features resides in a vascular dilating device having a pistol grip handle construction which imparts a mechanical advantage in effecting the plunger displacement enabling the operator to attain and maintain very high pressures with a minimum of effort or force.

Another feature resides in the provision of a valve assembly which permits the balloon catheter to be readily and quickly deflated.

Another feature of this invention resides in the provision wherein the unidirectional valve construction may be variously formed.

Another feature of this invention resides in the provision wherein the pistol grip handle construction may be variously formed to impart one hand operation and a mechanical advantage necessary to attain the desired high pressures.

Other features and advantages will become more readily apparent when considered in view of the drawings and detailed description thereof.

FIG. 2 is a partial exploded perspective view illustrating the component parts of FIG. 1.

FIG. 3 is a detailed sectional view of the valve assembly embodied in FIG. 1 showing the parts in a balloon inflating position.

FIG. 3A is a section view taken on line 3A—3A of FIG. 3.

FIG. 4 is a section view of the valve assembly of FIG. 3 in a balloon inflating position.

FIG. 5 is a side view of a modified embodiment of the invention.

FIG. 6 is a side view of yet another embodiment of the invention.

DETAIL DESCRIPTION

Figure 1:
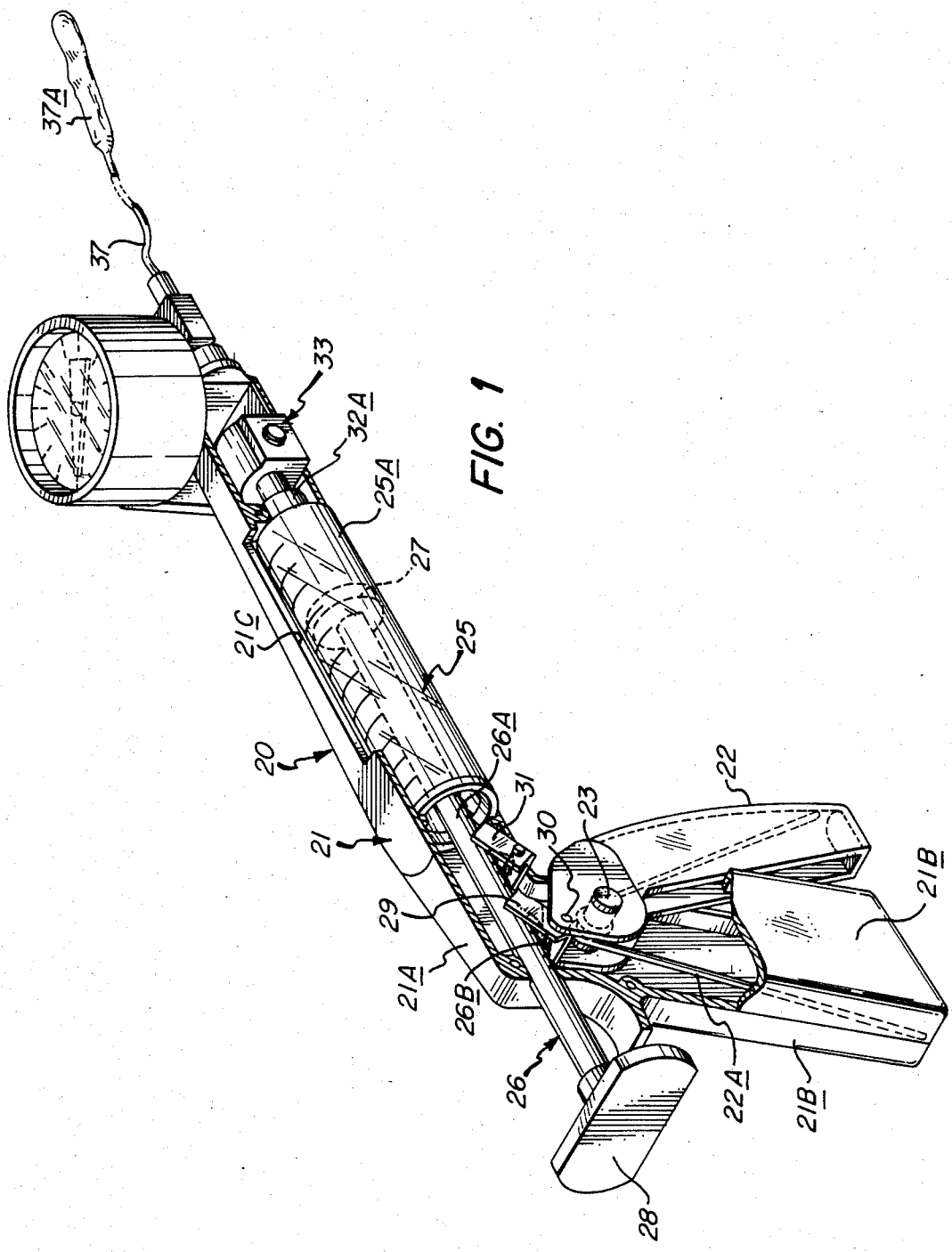
FIG. 1 is a perspective view of a vascular dilating device embodying the invention.

Referring to the drawing viz. FIGS. 1 to 3 there is disclosed a vascular dilating device 20 for use in an angioplasty procedure. The illustrated device 20 of FIGS. 1 to 3 comprises a housing 21 which may be formed as a pair of similar complimentary members for enclosing the internal components of the device. As shown in FIG. 1, only one of the complimentary housing section 21A is illustrated. The other complementary housing portion or section has been removed to show the internal components.

The respective housing sections 21A are each formed with a longitudinally extended portion to define an enclosure for housing a syringe assembly 25 as will be hereinafter described. The rear end of the respective housing sections 21A defines a pistol type handle 21B to which an actuating lever or trigger-like mechanism 22 is pivoted about a pivot pin 23.

Disposed between the complementary housing sections 21A is a syringe assembly 25 which comprises a 10 cc syringe body or barrel 25A and an associated plunger 26. Preferably, the syringe barrel 25A may be made of a clear or transparent material having graduated indicies so as to indicate the amount of actuating fluid in the syringe barrel 25A. It will be understood that a fluid tight piston 27 is provided on the inner end of the plunger 26 and which is disposed in sliding relationship to the internal surface of the syringe barrel 25A. In accordance with this invention, the lower sector of the plunger shaft 26A is serrated to define a series of spaced ratchet like teeth 26B. The outer end of the plunger shaft 26A is provided with an end cap 28 by which the plunger shaft 26A may be readily grasped for manual retraction and/or to rotate the shaft as will be herein described to disengage the ratchet teeth 26B from the driving pawl 29.

The driving or ratchet pawl 29 is connected to the trigger 22 about a pivot 30, and is spring loaded. The ratchet pawl 29 thus functions to effect the drive of the plunger 26 when engaged with the ratchet teeth 26B, each time the trigger 22 is squeezed. A second pawl 31 is pivoted to the housing 21A to prevent any back lash of the plunger and to maintain the plunger in its incremental advanced position as the trigger 22 is released to reset the driving pawl 29 for next successive actuation. The lever or trigger is preferably spring bias by a suitable spring member 22A.

Connected to the outlet end 32 of the syringe assembly or syringe barrel 25A is a valve assembly 33. As best seen in FIG. 2, the valve assembly 33 comprises a valve body 34 having an inlet 35 provided with a Luer or quick type connect 35A whereby it can be readily detachably secured to a complementary fitting connected to the outlet end 32 of the syringe barrel 25A.

The outlet end 36 of the valve assembly 33 has detachably coupled thereto a balloon catheter 37 of well known construction. U.S. Pat. No. 4,332,245 discloses such balloon type catheter. As best seen in FIG. 2, the end 37A of the balloon catheter is provided with a Luer type fitting for effecting a quick detachable connection with the outlet end 36 of the valve assembly 33.

Figure 10:
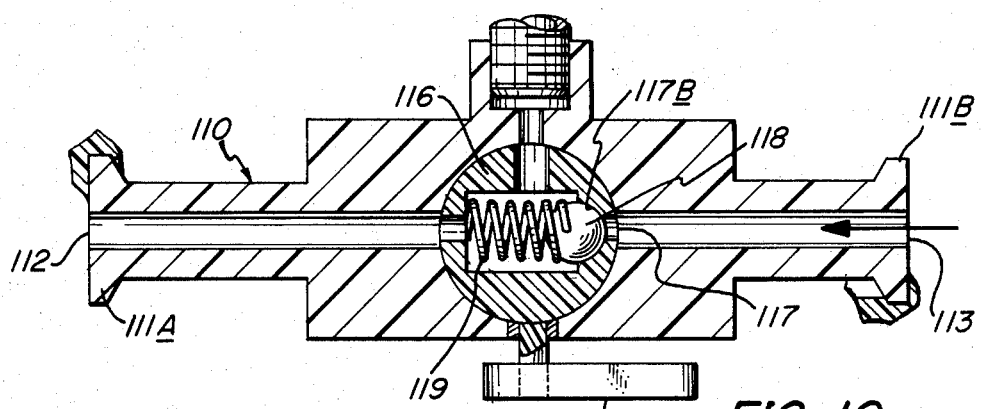
FIG. 10 is a section view of the embodiment of FIG. 9 showing the parts in a balloon deflating position.

Referring to FIG. 3 of the drawing, the valve body 34 is provided with a passageway 38 which communicates the reservoir portion of the syringe body 25A to a valve chamber 39 disposed intermediate the ends of the valve body 34. The valve chamber 39 in turn is connected in communication to the attached balloon catheter by passageway extension 38A. Disposed in communication with the passageway 38 are one or more passways 40, 41 and 42, which connect with the valve chamber. The chamber wall 39A to which the passways 40, 41 and 42 connect is provided with a valve seat 43. The arrangement is such that ends of the passway 40, 41, 42 are circumferentially spaced about the valve seat 43 as best seen in FIG. 10.

In the form of the invention thus far described, a unidirectional valve means is provided to valve the openings of the passways 40, 41, 42 circumscribed in the valve seat 43. The unidirectional valve means 44 comprises a flutter type valve having a valve head 45 formed as a flexible diaphram which is connected to a valve stem 46. As shown in FIG. 3, the valve stem 46 is fixedly secured in a bore 47 formed in the valve body so that the valve head 45 is firmly seated in the valve seat to seal off the openings of the passways 40, 41, 42 to the valve chamber. The arrangement is such that the unidirectional valve means 44 will permit fluid to flow only from the syringe barrel to the balloon catheter when the plunger is displaced, and prohibits any reverse flow of the fluid from the balloon catheter back to the syringe barrel.

To control the direction of fluid flow to and from the catheter, there is provided a control valve means 48. The control valve means 48 comprises a rotary valve 48A rotatably journaled in a bore 49 which extends transversely of the passageway 38. Connected to the rotary valve 48A is a handle 48B by which the rotary valve may be rotated between a first and second position. As shown in FIG. 3, the rotary valve 48A is provided with a transverse bore or pass 50 which, in one position of the rotary valve, connects the passway 38 to passageway extension 38A via passways 40, 41, 42, causing the actuating fluid to flow from the syringe barrel 25A to the balloon catheter when the trigger or actuating lever 22 is actuated. The rotary valve 48A is also provided with a radial bore or port 51 which intersects with the transverse bore or pass 50. In the illustrated embodiment, the radial port 51 is disposed at substantially right angle to the transverse bore 50.

The arrangement of the control valve 48A is such that rotation of the valve from a balloon inflating position as seen in FIG. 3, to a balloon deflating position as seen in FIG. 4, causes the transverse port 50 and radial port 51 to be displaced so as to connect a by-pass channel 52 to the syringe barrel 25A.

The by-pass channel has one end 52A in communication with the valve chamber 39 and its other end 52B with the bore 49 of th rotary valve 48A. Thus, the end 52B of the bypass 52 is arranged to be valved by the rotary valve 48A between an open and closed position. As will be hereinafter described, the bypass 52 is arranged to direct the flow of actuating fluid around the unidirectional valve means 44; when the rotary valve 48A is disposed in a balloon delfating position (See FIG. 4.)

Connected in communication with the valve chamber 39 on the pressurized side thereof is a pressure gauge 53, whereby the fluid pressure imparted on the balloon catheter can be readily noted by the pressure gauge indicator 53A.

The operation of the vascular dilating device 20 described is as follows:

The syringe barrel 25 is first loaded with an actuating fluid, e.g. saline solution or other suitable liquid medium. This is effected by attaching a filling needle (not shown) to the front end of the syringe barrel and asperating the actuating fluid from a sterile source into the syringe barrel 25A by pulling back on the plunger 26. With the syringe barrel 25A thus filled with actuating fluid or liquid; the air within the syringe barrel 28A, if any, is expunged by advancing the plunger slightly in a well known manner. With the air expelled, the filling needle is removed and the balloon catheter is attached to the end of the syringe barrel 25A.

With the device 20 filled with actuating fluid and the balloon catheter 37 attached, the device 20 is readied for the performance of an angelopastic procedure. The operating surgeon then inserts the deflated catheter into the blocked blood vessel until the balloon tip 37A or end of the catheter reaches the occluded portion. The catheter is then inflated and held to a specific pressure, as determined by the surgeon for 30 to 90 seconds. This is attained by the surgeon rotating the rotary valve 48 to the balloon inflating position, i.e. rotating the control valve 48A to align the transverse valve port 50 with passageway 38 and its extension 38A. In this position as shown in FIG. 3, the end 52B of the bypass channel 52 is closed. With the plunger ratchet teeth 26B rotated to effect engagement with the ratchet pawl 29, the actuation of the lever or trigger 22 will cause the plunger to advance and express the fluid from the syringe barrel 25A to passageway 38, through the rotary valve port 50, past the unidirectional valve means 45 and into the balloon catheter to inflate the balloon portion thereof in incremental amounts. As it will be evident, the displacement of the plunger and its piston 27 will cause the flexible valve head 45 to be slightly displaced from its valve seat causing fluid to flow from passways 40, 41, 42 and to the balloon catheter. Upon release or cessation of the force applied to the trigger, the back pressure of the fluid in the balloon catheter acting on the valve head 45 of the unidirectional valve means 44 will seat the diaphram head 45 flush against the valve seat to seal off passways 40, 41, and 42. Thus, the fluid is prohibited from flowing out of the balloon catheter and the pressure acting on the balloon catheter is maintained until released; all without any effort on the part of the operator. With the arrangement described, a surgeon can readily build up the pressure within the balloon catheter as may be required to clear the blockage. Pressures ranging from 0 to 450 psi can thus be readily attained without effort by the surgeon, and by using only one hand.

To release the fluid pressure of the balloon catheter, the surgeon need only to slightly retract the plunger which subjects the syringe barrel to a negative pressure. Then the surgeon need only to rotate the rotary valve 48A ninety degrees or to the balloon catheter deflating position (FIG. 4). Such rotation shifts the valve ports 50 and 51 to a position whereby the bypass or channel 52 is opened to permit the fluid to flow from the catheter to the syringe barrel 25A and thereby effect an immediate and almost instantaneous deflation of the balloon catheter; which is highly desirable in an angioplastic procedure. The arrangement of the plunger 26 is such that the ratchet teeth 26B can be readily engaged and disengaged from the ratchet pawl 29 or 31 by merely rotating the plunger shaft approximately 180°. With the ratchet teeth 26B so disengaged, the plunger 26 may be readily retracted or advanced manually by the surgeon as may be desired.

As shown in FIG. 1, the housing sections 21A are provided with a cut-out or window 21C adjacent the syringe barrel 25A, whereby the amount of fluid being expressed can be rendered readily visible to the surgeon.

It will be apparent that the balloon catheter can be readily inflated to effect very small increments of increases of pressure by the surgeon simply by squeezing the trigger or actuating lever 22 with a minimum of effort. The fluid pressure thus exerted by the balloon catheter on the occluded vein or artery is indicated by the pressure gauge. Also, the described device 20 maintains the desired pressure exerted by the balloon catheter, until released, without any effort on the part of the surgeon or user; because of the operation of the unidirectional valve means 44 described.

As it will also be apparent to those skilled in the art, the entire device can be inexpensively produced so that if desired, the entire device can be rendered readily expendible after use on a given patient, thus avoiding any danger of cross contamination.

While the device 20 is described as having a plunger formed with ratchet teeth and a complementary pawl drive means, it will be readily appreciated that the plunger may be actuated by a friction drive means. That is, a friction holding pawl acting on a smooth plunger shaft may be substituted in place of the ratchet teeth and pawl drive described.

FIG. 5 illustrates a modified form of the invention. In this form of the invention, the illustrated vascular dilating device 60 comprises a modified handle construction 61 with an associated syringe assembly 62, valve assembly 63 and attached balloon catheter 64. The syringe assembly 62 of this embodiment comprises a syringe barrel 62A similar to the syringe barrel 25A of FIGS. 1 to 3. Associated with syringe barrel 62A is a plunger 62B of general construction. The valve assembly 63 includes the control valve 63A and a unidirectional valve similar to the valve assembly 44 hereinbefore described with respect to FIGS. 1 to 3. The balloon catheter 64 is also similar to that hereinbefore described.

In this form of the invention, the syringe assembly is suitably secured to a handle member 61A of the handle means 61. As shown, the handle member 61A is provided with an opening 65 disposed intermediate the ends of the handle member 61A to which the syringe barrel is suitably fitted or connected. Connected to the upper end of the fixed handle member 61A is a laterally projecting rack 66. As shown, the rack 66 comprises a bar having an elongated continuous slot 67 formed therein. The slot 67 includes a series of spaced apart indentations or sub recesses 67A formed therein. As shown in FIG. 4, the respective indentations or sub recesses provide a bearing seat for receiving the pivot pin 68, by which an actuating lever 69 is rendered pivotally connected to the rack 66 for movement toward and away from the fixed handle member 61A.

As shown, the actuating lever 69 is provided at its upper end with a bifurcated portion 69A whereby the bifurcate end straddles the rack 66 therebetween. The pivot pin 68 is adapted to be received in one of the selected indentations 67A. Thus, the lever 69 can be adjustably positioned relative to the fixed handle member by shifting the position of the pivot pin 68 to rest in a particular indentation 67A. The actuating lever is also provided with a bearing portion 70 which is adapted to bear on the end 62C of the syringe plunger 62B. From the construction described, it will be apparent that when the lever 69 is squeezed toward the fixed handle member 61A, the plunger 62 is displaced into the syringe body or barrel 62A to express the actuating fluid therein into the balloon catheter in a manner similar to that hereinbefore described. If desired, the plunger 62B can be normally biased against the actuating lever 69 by a coil spring 71 disposed about the portion of the plunger extending beyond the barrel 62A and the end 62C of the plunger 62. The device 60 is functional even without the coil spring 71.

In this form of the invention, a pressure gauge 72 is also associated with the valve assembly 63 as hereinbefore described.

With the exception of the handle construction 61 described, the operation and function of the device of FIG. 5 is virtually identical to the operation and function described with respect to FIGS. 1 to 3. In the form of FIG. 5, the handle construction is such that the actuating lever 69 and finger grip portion 61A can be gripped and squeezed by one hand to express the fluid necessary to inflate the balloon catheter in a continuous incremental manner as the plunger 62B is displaced into the syringe barrel 62A. Upon release of the force applied to the actuating lever 69, the spring 71 acting on the plunger 62B will automatically retract the plunger 62B and associated piston to subject the syringe barrel to a negative pressure. Thus, to deflate the balloon catheter, the rotary valve 63A is merely set to its balloon deflating position to open the valve bypass as hereinbefore described. With the construction of the embodiment of FIG. 5 described, it will be apparent that a surgeon can readily control the inflation and deflation of the balloon catheter 64 by coordinating the squeezing of the handle members 61A and 69 and the positioning of the control or rotary valve 63A between the balloon inflating and deflating position in a precise and accurate manner to insure a successful angioplastic procedure, and whereby the response of the balloon catheter is rendered virtually instantaneous. Also, the applied force or mechanical advantage which is desired to be applied to the end of the plunger 62B can be varied or adjusted by shifting the pivot pin 68 of the actuating lever 69 to a particular indentation 67A. With the construction described, the shifting of the pivot pin 68 can be readily achieved by shifting the lever 69 relative to the rack 66 to lift the pin 68 over the ridge 67B between successive indentations 67A. The handle construction 61 thus provides the surgeon with the desired mechanical advantage to attain the desired high pressures and whereby the achieved pressures can be maintained without effort on the part of the surgeon; since the pressures developed are held by the action of the unidirectional valve incorporated in the valve assembly 63 as hereinbefore described, until released by actuation of the control valve 63A.

FIG. 6 illustrates a further modified form of the invention. In this form of the invention, the vascular dilating device 80 includes essentially the components of a handle construction 81, a generally conventional 10 cc B-D type syringe assembly 82, a valve assembly and a balloon catheter as described. In this form of the invention, the valve assembly includes a control valve and unidirectional valve, and balloon catheter, all constructed similarly to that hereinbefore described.

In this form of the invention, the fixed handle member 81A is provided with a construction by which the lateral finger grip 82A of a conventional 10 cc B-D syrine body 82B can be detachably connected thereto. With the syringe barrel 82B so connected to handle member 81A, the associated plunger 82C of the syringe assembly extends rearwardly thereof. In this form of the invention, the actuating lever 81B of the handle construction is pivotally connected by a pin 85 to the upper end of handle member 81A. As shown, the actuating lever 81B is provided with a bearing portion 81C which is adapted to receive or bear on the end 82D of the plunger 82C. The fixed handle member 81A is also provided with an elongated opening or slot 86 to provide a finger opening therein whereby the surgeon can grip the device 80 with the lever 81B bearing against the surgeon's palm. It will thus be apparent that as handle or lever member 81B is squeezed or displaced toward the fixed handle member 81A, that the plunger 82C is forced into the syringe barrel 82B to express the actuating fluid therefrom. A coil spring 86 disposed about the extended end of the plunger 82C and exerting a spring bias on the head end 81D of the plunger normally forces the plunger 82C toward its retractable position, and against the lever member 81B.

In the illustrated embodiment, the bearing portion 81C is convexly formed to define a bearing arc which bears on the headed end 82D of the plunger 82C as the actuating lever is moved relative to the fixed handle member 81A.

In operation, the device of FIG. 6 is similar to that described with respect to the device of FIG. 5. The devices 60 and 80 are filled with the appropriate amount of actuating fluid as described with respect to FIGS. 1 to 3. With the air purged, the filling needle is removed and the balloon catheter attached. The angioplastic procedure is then followed with the devices 60, 80 as hereinbefore described. The respective handle construction of FIGS. 5 and 6 enables the user to incrementally increase to balloon pressure with absolute control in a desired repetitive manner to clear the obstruction in the vascular vessel. With the construction described, the surgeon need not physically maintain the pressure in the balloon catheter. This is because the utilization of the unidirectional valve in the valve assembly prohibits the exertion of any back pressure of the fluid inflating the balloon catheter from acting on the actuating lever of the device. Thus, a surgeon can release the actuative lever, and the fluid pressure will still be maintained on the balloon catheter until release by shifting the control or rotary valve to open the bypass of the valve assembly as hereinbefore described. It will be understood that a pressure indicator or gauge may be operatively associated with the valve assembly, as previously described.

Figure 7:
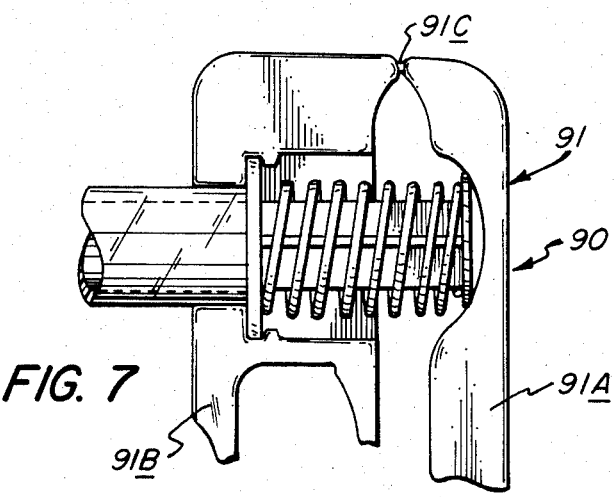
FIG. 7 is a side view of still another embodiment of the invention.

FIG. 7 illustrated a further modified embodiment of a vascular inflating device 90. This form of the invention is virtually identical to the devices 60 or 80 with the exception that the handle construction 91 is somewhat modified. In this form of the invention, the actuating lever 91A is integrally connected to the fixed handle member 91B by a "living" or integrally molded hinge portion 91C. Such handle construction 91 can be readily molded of a suitable plastic as a unitary member to further simplify the manufacture and/or assembly of the device. In all other respects, the device 90 is similar to that described and shown herein with respect to FIGS. 5 or 6. That is, the syringe assembly, valve assembly, associated pressure gauge and balloon catheter are all similar to that described herein. Like in FIG. 5, the utilization of a coil spring as, for example, 86 in FIG. 6 and spring 92 in FIG. 7, may be optional. In the event a coil spring is not used to bias the plunger, it is understood that the user would have to manually retract the plunger to subject the syringe to a negative pressure. In function and operation, the device of FIG. 7 is similar to that of FIGS. 5 or 6.

In this form of the invention, the handle portion 91 could be rendered reuseable with replaceable syringe assemblies and associated components, e.g. the valve assembly and balloon catheter, as evident with the construction of FIG. 6.

Figure 8:
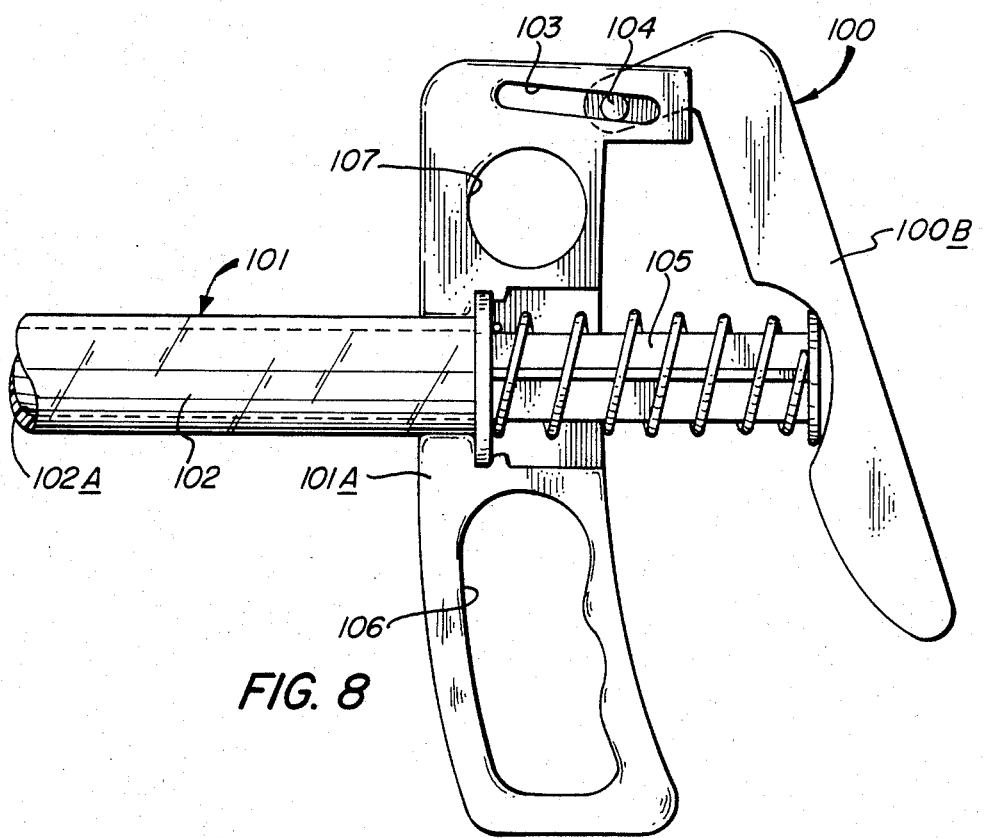
FIG. 8 is a side view of another modified embodiment.

FIG. 8 illustrates a further modified handle construction for use with a vascular dilating device embodying the invention described herein. In this form of the invention, the handle construction 100 of vascular device 101 comprises a fixed handle member 101A to which a generally conventional 10 cc B-D syringe assembly 102 is detachably connected or secured. The upper end of the fixed handle member is provided with a slotted opening 103 for slidably receiving therein a pivot pin 104 by which the actuating lever 100B is pivotably connected. In this form of the invention, the plunger 105 of the syringe assembly 102 is disposed in bearing relationship to the actuating lever 100B. Thus, as the actuating lever 100B is actuated, the plunger 105 is displaced relative to the syringe barrel 102A, accordingly. Like the device of FIG. 6, the fixed handle member 100A is provided with finger openings 106 and 107 located above and below the connected syringe assembly 102. This embodiment, like those of FIGS. 4, 5 and 6, has the end of the syringe plunger 108 disposed in bearing or camming relationship with the actuating lever 100B. It will be understood that the discharge or outlet of the syringe barrel 102A is connected to a valve assembly and associated pressure indicator similar to that herein described with respect to FIGS. 1 to 3. Also, the balloon catheter connected to the valve assembly is likewise similar as hereinbefore described. In function and operation, the device 101 of FIG. 8 is similar to that of FIGS. 5, 6 or 7.

Figure 9:
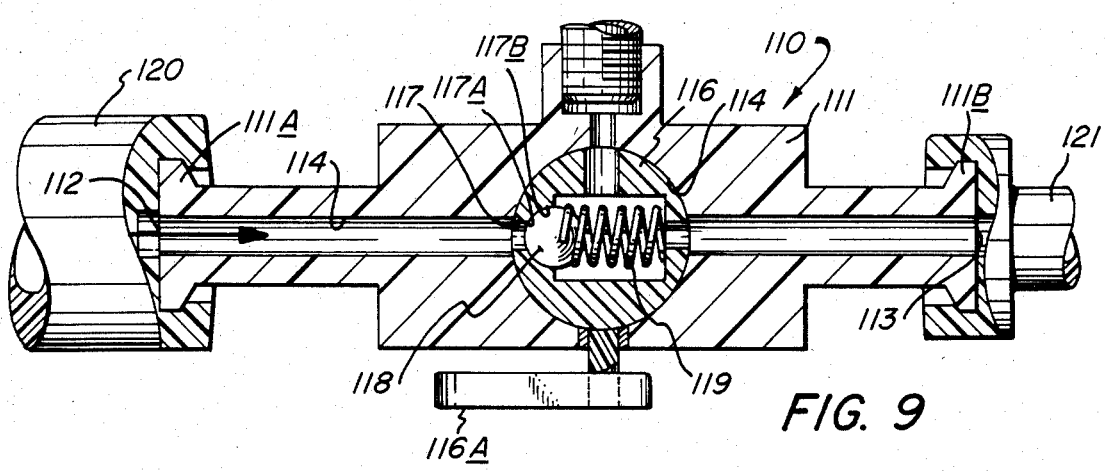
FIG. 9 is a detailed side view of a modified valve assembly for use in the disclosed embodiments showing the parts in a balloon inflating position.

FIG. 9 is directed to a modified construction of a valve assembly for controlling the flow of actuating fluid between the syringe assembly and associated catheter. In this form of the invention, the valve assembly 110 includes a valve body 111 which is provided with a Luer or quick connected coupling 111A, 111B at the inlet 112 and outlet end 113 thereof, respectively. Extending normal to the passageway 114 extending through the valve body 111 between the inlet 112 and outlet 113 is a bore 115 for rotatably receiving a rotary valve member 116. The rotary valve member 116 is provided with a diametric extending passway 117 extending therethrough for connecting the opposed ends of the passageway 114. One end 117A of the passway 117 is provided with a valve seat 117B. Disposed in the passway 117 is a valve 118 which is normally urged by spring 119 against the valve seat 117B to close end 117A of the passway 117. With the valve assembly 110 disposed between the syringe assembly 120 and the balloon catheter 121, the actuating fluid is normally prevented from flowing through the valve assembly until a force or pressure is applied to the fluid to overcome the force of spring 119. A pressure gauge or indicator is connected in communication with the outlet side of the unidirectional valve 118.

With the valve assembly 110 described, it will be apparent that as the piston or plunger of the syringe assembly 120 is activated, the displacement thereof will develop a pressure sufficient to overcome the force of spring 119 causing the valve member 118, illustrated as a ball valve, to be displaced permitting fluid flow to be directed to the catheter. Upon release of the force applied to the plunger, the spring 119 will urge the valve member 118 to reseat against the valve seat 117B to seal off the fluid flow and maintain the pressure in the catheter until released.

To release the pressure developed in the catheter or to deflat the same, the rotary member 116 containing the unidirectional or ball valve 118 is rotated 180°. See FIG. 10. In doing so, the pressure of the fluid in the balloon catheter, being greater than the force exerted by spring 119, causes the valve member 118 to unseat allowing the fluid in the catheter to be returned to the syringe barrel, as the latter is under a negative pressure.

It will be understood that the alternative valve assembly 110 described can be utilized in the devices of FIGS. 1 to 8 in lieu of the valve assembly depicted and described with respect thereto. While the unidirectional valve in FIGS. 9 and 10 is illustrated as a ball valve, other types of unidirectional valve shapes may be used in lieu of the ball type. For example, the unidirectional valve described in FIG. 3 may be substituted for the ball valve.

Figure 11:
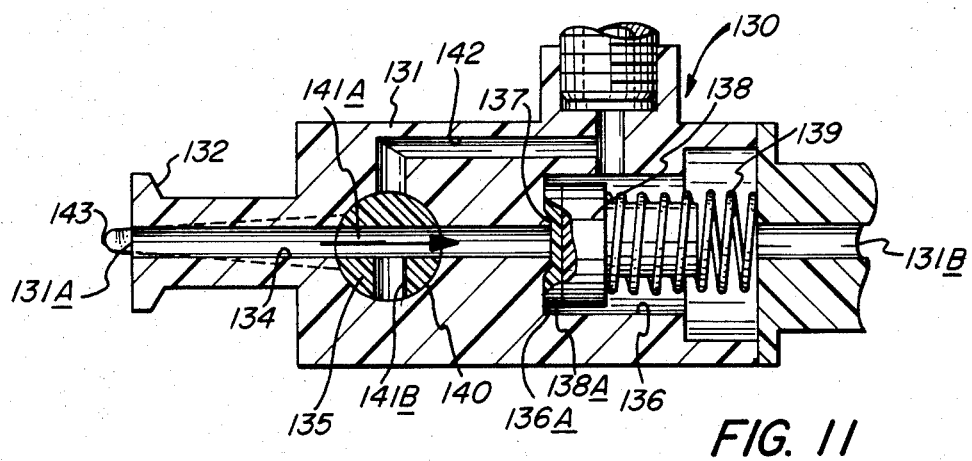
FIG. 11 is a sectional view of another modified valve assembly for use in the disclosed vascular dilating devices.

Another alternative unidirectional valve assembly is illustrated in FIG. 11. In this form of the invention, the valve assembly 130 includes a valve body 131 having an inlet end 131A provided with a quick disconnect coupling or end 132 by which the valve body can be detachably connected to the outlet of a syringe assembly; as hereinbefore described. The outlet end 131B is likewise provided with a fitting by which it can be detachably connected to a balloon catheter (not shown), but similar to that hereinbefore described. A fluid flow passageway 134 extends between the inlet 131A and outlet 131B which is interrupted by a rotary control valve member 135. Disposed within the valve body 131 in communication with passageway 134 is a valve chamber 136 having a wall portion 136A circumscribing the passageway 132. The end wall 136A adjacent the outlet of the passageway defines a valve seat 137. Disposed in the valve chamber 136 is a unidirectional valve member 138 having a valve head 138A which is normally maintained seated against the valve seat 137 to close the end of passageway 134. A spring 139 normally biases the valve member 138 against the valve seat 137.

Intersecting the passageway 134 is a bore 140 in which a rotary valve member 135 is rotatably journalled. The rotary valve member 135 is provided with a diametric extending port 141A and a radial port 141B connected to the diametric port similar to the rotary control valve member of FIGS. 1 to 3. The diametric extending port 141A is arranged to connect the inlet of passageway 134 to the outlet of passageway 131B when the rotary control valve member 135 is disposed in the catheter inflating position as shown in FIG. 11.

The valve body 131 is also provided with a bypass or channel 142. The bypass or channel 142 extends around the unidirectional valve member 138 to connect the bore 140 to the valve chamber 136 on the catheter side of the unidirectional valve. Thus, when the rotary or control valve 135 is rotated to a catheter deflating position, the radial port 141B is disposed in communication with the bypass or channel 142 to connect the catheter in communication with the syringe barrel so as to effect deflation of the catheter in a manner hereinbefore described.

Connected to the rotary or control valve member 135 is a handle 143 by which the rotary valve is actuated. The handle 143 may also function as an indicator to indicate to the surgeon or operator what mode the rotary valve 135 is positioned. For example, when the handle 143 is disposed parallel to the longitudinal axis of the syringe barrel, the catheter is readied for inflation. When the handle 143 is disposed normal to the axis of the syringe barrel, the catheter is in a deflating mode.

From the foregoing descriptions, it will be apparent that the valve assemblies described and handle constructions may be variously combined to define a given vascular dilating device. In whatever combination, the ultimate device enables the doctor or surgeon to precisely control the fluid pressures developed in the catheter with a minimum of effort because of the mechanical advantage afforded by the described handle constructions. Also, because of the unidirectional valve disposed between the syringe body and the catheter, the surgeon need not exert any manual force on the syringe plunger to maintain the fluid pressure on the catheter. The control valve, in conjunction with the bypass or channel around the unidirectional valve also provides the surgeon with a means for effecting almost instantaneous deflation of the balloon catheter which is extremely important in an angioplastic procedure. Also, the described devices and/or any variation thereof can be readily operated with one hand to achieve pressures not ordinarily possible by the prior known devices. The respective described devices are all capable of being readily manufactured in an extremely economical manner so that the devices can be rendered expendable after use; and thereby avoid any danger of cross contamination.

While the invention has been described with respect to several embodiments thereof, variations and modifications will become readily apparent to one normally skilled in the art without departing from the spirit or scope of the invention.

What is claimed is:

1. A vascular dilating device comprising a actuating means including means defining a fluid reservoir,
   a balloon catheter connected in communication with said fluid reservoir means,
   an unidirectional valve means interposed between said balloon catheter and said reservoir means,
   means defining a by-pass around said unidirectional valve means connecting said balloon catheter to said reservoir means, control valve means interposed between said reservoir means and said unidirectional valve means and said by-pass means whereby said control valve is operative in a first position to direct fluid flow through said unidirectional valve to inflate said balloon catheter and close said by-pass means, and operative in a second position to open said by-pass means to said reservoir means to deflate said balloon catherer.

2. A vascular dilating device as defined in claim 1 wherein said unidirectional valve means direct fluid flow from said reservoir means to said balloon catheter only.

3. A vascular dilating device as definded in claim 1 wherein said reservoir means includes a tubular barrel for containing a supply of actuating fluid,
   and a plunger having a piston connected thereto reciprocally mounted in said tubular barrel,
   and said actuating means including a handle means, and
   a lever pivotally connected to said handle means, said lever being in driving engagement with said plunger and connected piston for imparting a mechanical advantage in effecting the displacement of said plunger when said lever is actuated.

4. A vascular dilating device as defined in claim 1 wherein said unidirectional valve means comprises:
a valve body having a fluid passageway extending therethrough,
said passageway being disposed between said reservoir means and said balloon catheter and in communication therewith,
means defining a valve seat circumscribing said passageway,
a valve mounted to said valve body adjacent said valve seat to an open and closed said passageway for controlling the fluid flow therethrough.

5. A vascular dilating devise as defined in claim 4 wherein said valve body includes a bore intersecting said fluid passageway,
and said control valve comprising a rotary valve disposed in said bore,
and said rotary valve having port openings for connecting said passageway in communication with said reservoir and balloon catheter in one position of said rotary valve and a port opening connecting said by-pass to said reservoir in a other position of said rotary valve.

6. A vascular dilating device as defined in claim 4 and including a pressure gauge in communication with said passageway for indicating the fluid pressure therein.

7. A vascular device as defined in claim 3 wherein said plunger includes a series of ratchet teeth extending longilutionally thereof,
and said lever includes a ratchet pawl disposed in engagement with said ratchet teeth whereby the actuation of said lever permits incremental advancement of said plunger in said barrel each time said lever is actuated forcing the fluid in said barrel through said unidirectional valve means for inflating said balloon catheter.

8. A vascular device as defined in claim 7 of wherein said ratchet teeth are formed along only a circumferential portion of said plunger.

9. A vascular device as defined in claim 1 wherein said reservoir means includes a tubular barrel,
a plunger having a piston connected thereto reciprocally mounted in said tubular barrel;
and said actuating means including a handle means connected to said reservoir means,
a lever means
and means for adjustably pivoting said lever means to said handle means,
and said lever means being disposed in bearing relationship on said plunger whereby the pivoting of said lever means effects the movement of said plunger into said tubular barrel.

10. A vascular dilating device as defined in claim 9 wherein said means for adjustably pivoting said lever means comprises a rack connected to said handle means and extending laterally therefrom, said rack having a series of connected indentation formed therein, and said lever means including a fulcrum adapted to be adjustable received in one of said indentation about which said lever means is pivoted relative to said handle means.

11. A vascular dilating device as defined in claim 9 and including a means for normally biasing said plunger toward its retracted position.

12. A vascular dilating device as defined in claim 9 wherein said valve means includes a rotary valve having a fluid passageway extending through said rotary valve,
said passageway connecting said reservoir means in communication with said balloon catheter,
a valve seat disposed adjacent one end of said passageway,
a valve adapted to seat against said valve seat,
and a means for biasing said valve against said valve seat,
said valve being disposed so that in one position of said control valve fluid in directed into said balloon catheter for inflating the said and in a second position of said control valve, said valve effects deflation of said balloon catheter.

13. A vascular dilating device as defined in claim 12 wherein said valve means is unidirectional when disposed in either position of said control valve.

14. A vascular dilating device comprising,
a tubular barrel means defining a reservoir adapted to contain a supply of actuating fluid,
said barrel having an front opening end and a rear end,
a plunger having a piston connected thereto slidably mounted in said tubular barrel, said piston being in fluid sealing relationship with said barrel, and said plunger extending through said rear end of said barrel,
a unidirectional valve means connected to said front opening end, and said unidirectional valve means having an inlet and an outlet, and
said inlet being connected with the front opening end of said tubular barrel,
a balloon catheter connected with said outlet,
means defining a bypass to connect said balloon catheter with said reservoir,
a control valve means connected to said tubular barrel, balloon catheter and said by pass mean whereby in a first position of said control valve fluid flow is directed from said reservoir through said unidirectional valve means to said balloon catheter to inflate said balloon catheter, and in a second position of said control valve means said balloon catheter is placed in communication with said reservoir through said by pass means to deflate said balloon catheter,
and handle means associated with said tubular barrel and said plunger,
said handle means including a fixed handle member associated with said barrel, and a actuating handle member pivotally connected to said fixed handle member,
said actuating handle member being disposed in engaging relationship with said plunger whereby the movement of said actuating handle member relative to said fixed handle member effects the displacement of said plunger to force said actuating fluid through the front end opening of said barrel,
and means for normally biasing said plunger toward said moveable handle member.

15. A vascular dilating device as defined in claim 14 wherein said fixed handle member and movable handle member comprising a unitary molded member interconnected by a flexible hinge.

16. A vascular dilating device as defined in claim 14 wherein said fixed handle member includes a opening extending longitudinally thereof to provide a finger opening for grasping said fixed handle.

17. A vascular dilating device as defined in claim 14 wherein said fixed handle member includes means for detachably connecting thereto said tubular barrel.

18. A vascular dilating device comprising a housing,
a tubular barrel disposed in said housing,
said tubular barrel defining a reservoir adapted to contain a supply of actuating fluid,
said tubular barrel having a front end opening and a rear opening,
a plunger having a piston connected thereto, said piston being in fluid sealing relationship with said tubular barrel whereby said plunger and connected piston are reciprocally mounted in said tubular barrel for movement between a retracted and protracted position,
said plunger extending beyond the rear end of said tubular barrel,
a valve assembly connected in communication with said front opening of said tubular barrel,
said valve assembly including a valve body,
a valve chamber formed in said valve body, said valve chamber having a fluid outlet,
a passageway disposed in said valve body connecting said front end opening in communication with said valve chamber,
a bore extending transversely of said passageway,
a rotary control valve rotatably mounted in said bore,
a by-pass interconnecting said valve chamber with said bore,
a valve seat circumscribing said passageway adjacent said valve chamber,
a balloon catheter connected to the outlet of said valve chamber,
and a unidirectional valve connected to said valve body and engaging said valve seat for valving said passageway whereby fluid can flow therethrough for inflating the balloon catheter only,
said rotary control valve having a first passway for directing fluid flow from said reservoir to said valve chamber in a first position for inflating said balloon catheter, and said rotary control valve having a second passway for connecting said balloon catheter to said reservoir in a second position for deflating said balloon catheter,
and said housing including a first handle member connected thereto,
a movable actuating handle member pivotally connected relative to said first handle member,
means for drivingly connecting said movable actuating handle member to said plunger whereby the operation of said movable actuating handle member effects incremental displacement of said plunger and connected piston relative to said reservoir.

19. A vascular dilating device as defined in claim 18 and including means for disengaging the driving connection between said plunger and said actuating handle member whereby said plunger can be retracted independently of said actuating handle member.

20. A vascular dilating device as defined in claim 18 wherein said unidirectional valve comprises a flexible diaphragm that permits fluid to flow through said passageway in one direction only.

21. A vascular dilating device as defined in claim 18 and including a pressure gage connected to said valve chamber.

22. A vascular dilating device comprising,
an actuating means including a reservoir means for containing a supply of actuating fluid,
a piston means reciprocally mounted in said reservoir means,
a balloon catheter connected to said reservoir means,
a control valve connected between said reservoir means and said balloon catheter,
a by-pass means connected between said reservoir means and said balloon catheter whereby in one position of said control valve, said reservoir means is disposed in communication with said balloon catheter for inflating said balloon catheter, and in a second position of said control valve, the balloon catheter is connected in communication with said by-pass means to deflate said balloon catheter, and
a unidirectional valve means operatively associated with said control valve for maintaining the pressure of the fluid acting on said balloon catheter during inflation of said balloon catheter independently of said actuating means when said control valve is in said one position.

* * * * *